United States Patent [19]

Ball

[11] Patent Number: 4,750,351
[45] Date of Patent: Jun. 14, 1988

[54] IN-LINE VISCOMETER

[75] Inventor: John M. Ball, Huntsville, Ala.

[73] Assignee: The United States of America as represented by the Secretary of the Army, Washington, D.C.

[21] Appl. No.: 82,763

[22] Filed: Aug. 7, 1987

[51] Int. Cl.[4] .......................................... G01N 11/08
[52] U.S. Cl. ........................................... 73/55; 73/54
[58] Field of Search .................. 73/54, 55, 56; 137/92

[56] References Cited

U.S. PATENT DOCUMENTS

| 2,771,770 | 11/1956 | Bouman | 73/55 |
| 2,896,656 | 7/1959 | Allen et al. | 137/92 |
| 3,938,369 | 2/1976 | DeBok | 73/55 |
| 4,680,957 | 7/1987 | Dodd | 73/55 |

FOREIGN PATENT DOCUMENTS

| 858031 | 12/1952 | Fed. Rep. of Germany | 73/55 |
| 1168123 | 4/1964 | Fed. Rep. of Germany | 73/55 |
| 155740 | 9/1984 | Japan | 73/54 |
| 746340 | 3/1956 | United Kingdom | 73/55 |
| 1233002 | 5/1986 | U.S.S.R. | 73/54 |

OTHER PUBLICATIONS

"Instruments for Controlling Viscosity and Consistency", Table 22-18, John H. Perry, Chemical Engineers Handbook, 1963.

Primary Examiner—Stewart J. Levy
Assistant Examiner—Hezron E. Williams
Attorney, Agent, or Firm—John C. Garvin, Jr.; Freddie M. Bush

[57] ABSTRACT

An in-line viscometer comprising in combination a flowsection, a flowmeter installed to measure flow through the flowsection, a friction flow tube installed parallel and suspended within the flowsection and having pressure ports on the respective entrance and exit ends of the friction flow tube. The pressure ports communicates with a meter for determining the differential pressure between the entrance port and exit port. The described structure provides the necessary values for determining viscosity in accordance with the following equation:

$$\mu = \frac{K_c (P_2 - P_1)}{\left[ \frac{\rho Q_T^2}{A^2} - 2(P_2 - P_1) \right]^2}$$

wherein $\mu$ is viscosity, $P_2 - P_1$ is differential pressure ($\alpha P$), $K_c$ is a calibration constant, $\rho$ is fluid density, $A$ is cross sectional area and $Q_T$ is flow rate through the friction flow tube and flowsection.

2 Claims, 1 Drawing Sheet

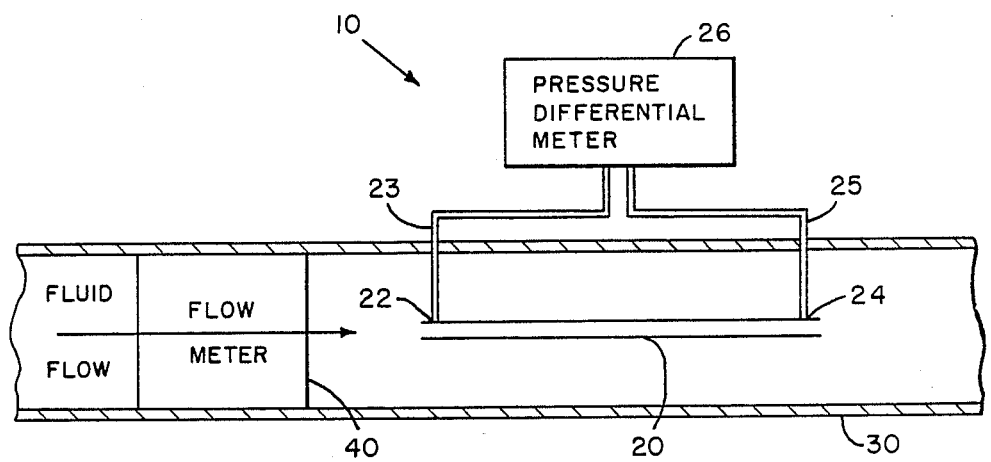

IN-LINE VISCOMETER

DEDICATORY CLAUSE

The invention described herein may be manufactured, used, and licensed by or for the Government for governmental purposes without the payment to me of any royalties thereon.

BACKGROUND OF THE INVENTION

Measuring viscosity has been a requirement for many industrial processes which have their beginning on a smaller scale such as in a laboratory. The several types of viscometers which are employed as control instruments are discussed below for background information.

Various instruments for controlling viscosity and consistency include viscometers such as the Saybolt which are based on timed discharge through nozzle which is commonly used for expressing viscosities of oils.

Timed fall of a ball or rise of a bubble is employed in a typical laboratory method for measuring oil viscosity.

A continuous consistency meter, such as the Fischer and Porter Company instrument, is based on a gear pump diverting a portion of product stream through a flow bridge where a pressure differential between two reference points is established. The differential pressure is a direct measure of the consistency of the materials.

Another type viscometer by Norcross Corporation employs a piston which is raised in a time sequence and falls by gravity through a liquid. Time of fall is recorded as a measure of viscosity.

A torque to rotate a torque element in a liquid is the principle employed in the Brookfield Engineering Company viscometer. In this viscometer a synchronous motor drives a vertical spindle with disk, paddle or cylinder submerged in a test liquid. Drive is through a calibrated spring. Angular lag of spindle behind motor is proportional to viscosity and is measured in various ways.

A viscosity-sensitive rotameter by Fischer and Porter Company employs rotameter bobs which are designed for either sensitivity or immunity to viscosity. With constant flow rate a sensitive bob can be calibrated for viscosity. One method is to use an immune bob to set flow at a series of index marks to measure viscosity by reference to the calibrated scale.

A viscometer which employs a friction tube outside the main stream of flow is used for a wide range of industrial liquids for remote recording and control. The pressure drop through friction tube is achieved where pressure drop across ends of tube is measured by pneumatic force-balance type differential pressure transmitter in terms of absolute viscosity. The results gives direct solution to Poiseville's equation. Thus, the liquid is pumped at constant rate through a friction tube in viscous flow to measure or determine viscosity.

The traditional methods of generating flow through a friction tube as a means for measuring viscosity described above require constant flow pumps, valves and fittings for taking a continuous sample from the process line; however, this method does not measure actual in-line conditions. Particularly, in measuring viscosity with a device which is subject to in-process fluid line conditions of pressure and temperature requires a special design. The lack of this special design has been a shortcoming of the prior art viscometers.

Therefore, an object of this invention is to provide a device which is truly an in-line viscometer which employs a friction tube.

A further object of this invention is to provide an inline viscometer, which by actually being installed in a process fluid line, is subjected to the same pressure and temperature that the fluid being measured is subjected to and the viscosity under the process conditions is thus accurately determined under the same conditions as the main stream flow conditions.

SUMMARY OF THE INVENTION

The in-line viscometer of the present invention comprises in combination: a flowsection, a flowmeter installed to measure flow through the flowsection, a friction flow tube having an entrance and exit end, the friction flow tube is sized to a predetermined size to achieve laminar flow when a viscous fluid is pumped through the flowsection and the friction flow tube installed within the flowsection, a pressure port on the respective entrance and exit ends of the friction flow tube, tubular member extending from each of pressure ports to a means to accurately measure the differential pressure (pressure differential meter) between entrance and exit pressure ports of the friction flow tube while flow through the flowsection and friction flow tube is taking place and while the friction flow tube is being subjected to the same temperature and pressure to which the flowsection is subjected.

The viscosity of the viscous fluid being measured relates to the differential pressure across the friction tube in the following relationship:

$$\mu = \frac{K_C(P_2 - P_1)}{\left[\dfrac{\rho Q_T^2}{A^2} - 2(P_2 - P_1)\right]^2}$$

wherein K is a calibration constant, $Q_T$ is the flow rate in flowsection, and $P_2 - P_1 = \Delta P$. In other words, the pressure across the friction flow tube is measured at the entrance and exit pressure ports of the friction tube, and this differential pressure is related to the flow rate in the flow tube and the fluid viscosity. Thus, viscosity is determined.

BRIEF DESCRIPTION OF THE DRAWING

The single Figure of the drawing depicts an in-line viscometer with associated parts shown in relationship to a mainstream flowmeter and flowsection.

DESCRIPTION OF THE PREFERRED EMBODIMENT

The in-line viscometer is comprised of a friction tube installed in a parallel relationship to a main stream flowsection, a pressure port at the entrance and exit end of the friction flow tube for determining the differential pressure, and a flowmeter for determining the flow rate in the tube of the main stream flowsection. The viscosity is determined from the equation:

$$\mu = \frac{K_C(P_2 - P_1)}{\left[\dfrac{\rho Q_T^2}{A^2} - 2(P_2 - P_1)\right]^2}$$

$\mu$ is viscosity, $P_2$ is pressure at entrance pressure port, $P_1$ is pressure at exit pressure port ($P_2 - P_1$ is $\Delta P$), $K_C$ is calibration constant, Δ is liquid density, A is cross sectional area of the main stream flowsection and $Q_T$ is flow rate in the Pipe or main stream flowsection when $Q^T/A$ is large compared to $(P_2 - P_1)$, this equation may be approximated by $$\mu = \frac{K_C(P_2 - P_1)A}{\rho Q_T}.$$

In further reference to the drawing, 10 is an in-line viscometer shown in relationship to associated parts which comprise a viscometer friction flow tube 20 installed in a parallel relationship to the direction of flow in the main stream flowsection 30. An entrance end pressure port 22 and an exit end pressure port 24 is illustrated at the respective ends of the viscometer friction flow tube. Also shown is a means 26 to determine the differential pressure between the entrance end and pressure port and exit end pressure port of viscometer friction flow tube 20. Shown extending from respective ports to a pressure differential meter are tubing members 23 and 25. A means for measuring flow rate (flowmeter 40) is illustrated as an upsteam turbine flowmeter to establish the flow rate in the flowsection tube. The viscosity is determined from the relationship: differential pressure times the calibration constant, divided by the square root of the flow section velocity times the density minus twice the differential pressure across the friction tube.

Once the viscometer friction flow tube is installed, the calibration constant is determined, the flow rate in flowsection tube is determined, and the differential pressure is measured; then, the viscosity can be computed or recorded by any of several well established techniques for this type of mathematical relationship or computation.

Although the concise equation to compute viscosity is shown hereinabove, how this equation is developed or how it is evolved from the more complex equations should be of interest to the artisan of this field. The evolution of the concise equation including a calibration constant follows hereinbelow.

The equations are developed on the bases of the flow rate through the friction tube being laminar (which is true because of the appropriately sizing of the friction tube) and that impact pressure from the flow will force fluid through the friction tube.

If the fluid had zero viscosity, the velocity through the friction tube would be equal to the velocity of the fluid in the pipe, and there would be no pressure drop across the friction tube. If the fluid has any viscosity, a positive differential pressure will be generated across the friction tube.

Thus, from Bernoulli's Equation:

$$\frac{P_1}{\rho g} + \frac{1}{\rho 2g} V_1^2 = \frac{P_2}{\rho g} + \frac{1}{2g} V_2^2$$

it is recognized that a differential pressure will be produced due to the velocity in the friction tube, $V_2$, being less than the velocity in the pipe, $V_1$. It is also recognized that differential pressure across a friction tube is described by the Poiseuille Equation:

$$V_2 = K_p \frac{P_2 - P_1}{\mu}$$

wherein $K_p$ is a constant, and $\mu$ is the viscosity.

Since the product of the flow rate and viscosity in the friction tube is proportional to the differential pressure, the flow rate, differential pressure, and viscosity can be related. The actual equation was determined empirically. If the expression above for $V_2$ is substituted into the Bernoulli Equation, the simplified equation becomes $$\mu = \frac{K_C(P_2 - P_1)}{\left[\frac{\rho Q_T^2}{A^2} - 2(P_2 - P_1)\right]^{\frac{1}{2}}}$$

wherein $\mu$ is viscosity, $P_2 - P_1$ is differential pressure, $K_C$ is calibration constant, $\rho$ is the density, A is the pipe cross sectional area, and $Q_T$ is flow rate in flowsection tube.

The in-line viscometer has distinct advantages over the friction tube viscometers of the prior art. The distinct advantages include:

1. the in-line viscometer is actually in the process fluid line, subject to the pressure and temperature of the fluid being measured; this feature is a great advantage for highly viscous fluids which are sensitive to such effects;

2. the in-line viscometer is economical since it is intended for use in conjunction with a flow meter which would be installed anyway--although a dedicated flow meter could be used in a process line where flow rate was not being measured as part of process;

3. the in-line viscometer although it is illustrated with a turbine flow meter, any flow meter is workable with the in-line viscometer; in fact, any fixture or item subject to viscosity-induced changes in performance can be more accurate through the use of the in-line viscometer; and, 4. traditional methods of generating flow through a friction tube require constant flow pumps, valves and fittings into the process line; however, these methods do not measure actual in-line conditions as does the in-line viscometer.

I claim:

1. An in-line viscometer installed in a parallel relationship in a main stream flowsection which is to contain a viscous fluid which is to be pumped at a measured flow while the viscosity is to be determined by said in-line viscometer which is subjected to the same temperature and pressure that said main stream flowsection is subjected to while viscosity is being determined of said viscous fluid, said in-line viscometer comprising (i) a friction flow tube sized to a predetermined size so that viscous fluid flow through said friction flow tube is laminar and so that impact pressure from said viscous fluid flow forces said viscous fluid through said friction flow tube;

(ii) an entrance end pressure port and exit end pressure port at respective ends of said friction flow tube;

(iii) means for measuring viscous flow rate through said main stream flowsection; and, (iv) means for measuring pressure at said entrance end pressure port and said exit end pressure port to establish the diferential pressure between said entrance end pressure port and said exit end pressure port whereby the viscosity of said viscous fluid is determined from the equation:

$$\mu = \frac{K_C(P_2 - P_1)}{\left[\frac{\rho Q_T^2}{A^2} - 2(P_2 - P_1)\right]^{\frac{1}{2}}}$$

wherein $\mu$ is viscosity, $P_2$ is entrance port pressure of said viscous fluid, $P_1$ is exit port pressure of said viscous fluid, $K_C$ is a calibration constant, $\rho$ is fluid density, A is cross sectional area of said main stream flowsection, and $Q_T$ is flow rate in said main stream flowsection.

2. The in-line viscometer of claim 1 wherein said means for measuring pressure at said entrance end pressure port and said exit end pressure port comprises tubular members extending from each of said respective pressure ports for establishing communication with a pressure differential meter for determining $P_2$ - $P_1$ value of said equation.

* * * * *